US007899222B2

(12) United States Patent
Rinck et al.

(10) Patent No.: US 7,899,222 B2
(45) Date of Patent: *Mar. 1, 2011

(54) METHOD FOR SEGMENTATION OF ANATOMICAL STRUCTURES FROM 4D IMAGE DATA RECORDS

(75) Inventors: Daniel Rinck, Forchheim (DE); Michael Scheuering, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 941 days.

This patent is subject to a terminal disclaimer.

(21) Appl. No.: 11/220,666

(22) Filed: Sep. 8, 2005

(65) Prior Publication Data

US 2006/0159322 A1 Jul. 20, 2006

(30) Foreign Application Priority Data

Sep. 9, 2004 (DE) .................. 10 2004 043 677

(51) Int. Cl.
*G06K 9/00* (2006.01)

(52) U.S. Cl. .................. 382/128; 382/131; 382/132; 382/173

(58) Field of Classification Search .................. 382/100, 382/128–132, 154, 173, 254
See application file for complete search history.

(56) References Cited

U.S. PATENT DOCUMENTS

| | | | |
|---|---|---|---|
| 4,945,478 A * | 7/1990 | Merickel et al. ............. | 382/131 |
| 6,106,466 A * | 8/2000 | Sheehan et al. ............. | 600/443 |
| 6,169,817 B1 | 1/2001 | Parker et al. | |
| 7,095,890 B2 * | 8/2006 | Paragios et al. ............. | 382/173 |
| 7,379,572 B2 * | 5/2008 | Yoshida et al. ............. | 382/128 |
| 7,574,247 B2 * | 8/2009 | Moreau-Gobard et al. .. | 600/407 |
| 2003/0053667 A1 * | 3/2003 | Paragios et al. ............. | 382/128 |
| 2006/0210158 A1 * | 9/2006 | Pekar et al. .................. | 382/173 |

OTHER PUBLICATIONS

Matthew Brown, Michael McNitt-Gray, Nicholas Mankovich, Jonathan Goldin, John Hiller, Laurence Wilson and Denise Aberle, "Method for Segmenting Chest CT Image Data Using an Anatomical Model: Preliminary Results", IEEE Transactions on Medical Imaging, vol. 16, No. 6, Dec. 1997, pp. 828-839.*

(Continued)

*Primary Examiner*—Brian Q Le
*Assistant Examiner*—Eric Rush
(74) *Attorney, Agent, or Firm*—Harness, Dickey & Pierce, P.L.C.

(57) ABSTRACT

A method is disclosed for segmentation of anatomical structures, in particular of the coronary vascular system, from a sequence of 3D image data records recorded in a time sequence, in which the anatomical structure is first of all segmented from a first of the 3D image data records. In the method, during the segmentation of the anatomical structure, search areas of the segmentation are restricted and/or segmentation parameters associated with the three-dimensional relationships from the other 3D image data records are used, on the basis of known spatial conditions of the structure to be segmented, with respect to anatomical objects which are located in the surrounding area and of results of the segmentation from a respective next 3D image data record in the sequence from which the structure has already been segmented.

6 Claims, 2 Drawing Sheets

OTHER PUBLICATIONS

Xiaolan Zeng, Lawrence Staib, Robert Schultz and James Duncan, "Volumetric Layer Segmentation Using Coupled Surfaces Propagation", Computer Vision and Pattern Recognition IEEE 1998 pp. 708-715.*

Tim McInerney and Demetri Terzopoulos, "A Dynamic Finite Element Surface Model for Segmentation and Tracking in Multidimensional Medical Images with Application to Cardiac 4D Image Analysis" Computerized Medical Imaging and Graphics, vol. 19, No. 1, pp. 69-83, 1995.*

Tobias Boskamp et al, "New Vessel Analysis Tool for Morphometric Quantification and Visualization of Vessels in CT and MR Imaging Data Sets", Radiographics 2004, vol. 24, 287-297.

* cited by examiner

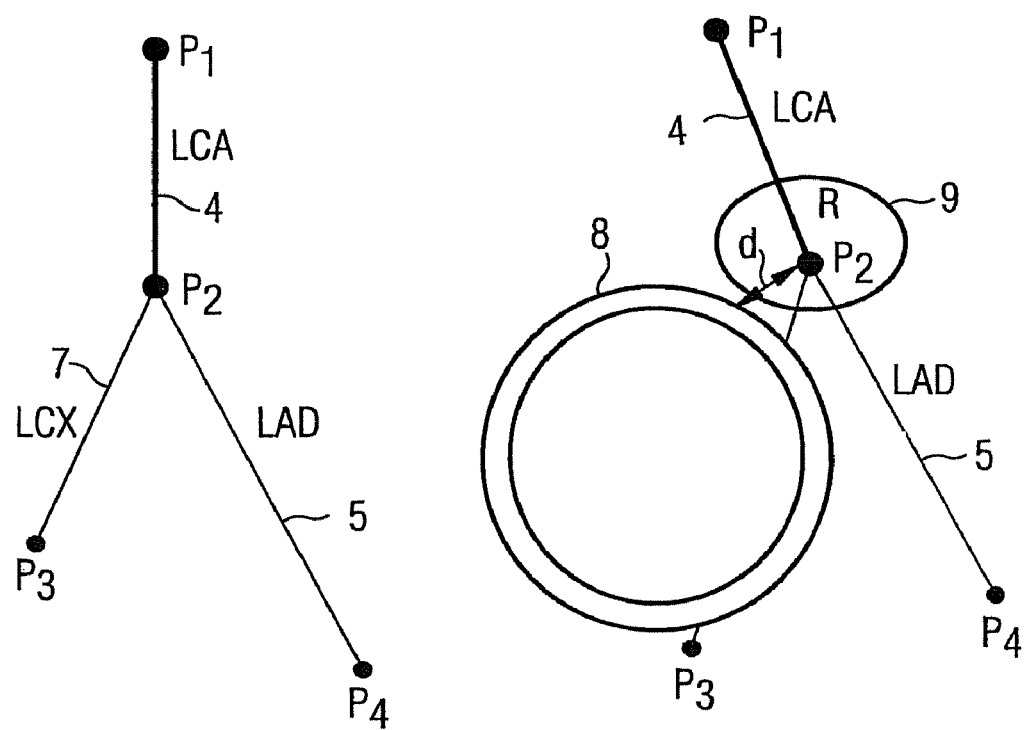

METHOD FOR SEGMENTATION OF ANATOMICAL STRUCTURES FROM 4D IMAGE DATA RECORDS

The present application hereby claims priority under 35 U.S.C. §119 on German patent application number DE 10 2004 043 677.0 filed Sep. 9, 2004, the entire contents of which is hereby incorporated herein by reference.

FIELD

The present invention generally relates to a method for segmentation of anatomical structures, in particular of the coronary vascular system, from a sequence of 3D image data records recorded in a time sequence, such as one, for example, in which the anatomical structure is first of all segmented from a first of the 3D image data records.

At least one embodiment of the present method is used in particular for recording vessel structures in the field of computed tomography (CT).

BACKGROUND

One major advantage of CT angiography in comparison to other imaging techniques such as magnetic resonance tomography (MR), PET (positron emission tomography), SPECT (single photon emission computed tomography) or 3D ultrasound is that, for example, the entire vascular system of the heart can be recorded in a single CT scan, by the use of contrast agent. The rapid further development of multilayer CT systems indicates that it will very shortly be possible to also image a plurality of phases of the heartbeat in the form of 3D data records in a short time sequence. The special diagnostic value of this technique is, in particular, that it is now possible to trace the entire heart anatomy from the diastolic state to the systolic state of the heart.

The examination of the coronary vessels (coronaries) is of particular interest in this case, since these can cause an inadequate supply to the myocardium, for example when plaque deposits result in a stenosis. This very frequently leads to a coronary infarct, and quite often to the death of the patient as well. For quantitative evaluation, in particular measurement of stenoses or plaque deposits, the appropriate areas of the vessel structure must be segmented from the 3D image data. Algorithm segmentation of the anatomical vessel structures, that is to say separation of the gray-scale values which represent the vessels in the 3D volume data record from the other anatomical structures, is therefore of major importance for the cardiological/radiological examination of the coronary vessels.

Various methods for segmentation of coronary vessels from 3D image data records are already known, such as techniques which are known by the expressions region growing technique, threshold value methods or level set methods. One example of a segmentation technique such as this for segmentation of vessel structures can be found in the publication by T. Boskamp et al., "New Vessel Analysis Tool for Morphometric Quantification and Visualisation of Vessels in CT and MR Imaging Data Sets" Radiographics 2004, 24, 287-297. However, when using algorithmic segmentation, surrounding tissue which does not belong to the coronary vessels is also frequently erroneously included in the segmentation process.

Based on the knowledge of the inventors, each individual 3D image data record is generally segmented independently of the others during the segmentation of vessel structures from a sequence of 3D image data records recorded in a time sequence, also referred to in the following text as a 4D image data record. This is a time-consuming and computation-intensive process for the segmentation of the 3D image data records for a complete heart cycle. However, tracing of the coronary vessel system in the time domain and thus segmentation of the individual 3D image data records from a sequence are actually highly important for functional evaluations of the heart.

U.S. Pat. No. 6,169,817 B1 describes a method for segmentation of anatomical structures from a sequence of 3D image data records recorded in a time sequence, which method is based on the idea of using segmentation results of a first 3D image data record for segmentation of the further 3D image data records in order to save computation time. In the method in this document, anatomical structures are first of all segmented from the first 3D image data record.

For the next step, it is necessary to know the elastic constants of the various segmented structures. A network of selected points is then formed, with which the appropriate constants are associated. Movement of each individual point to the next image is estimated on the basis of this network of points and the known material constants.

This recalculated network of points is then compared with this next image in order to produce a point-to-point correspondence by minimizing the total energy. In this way, the estimated movement of the individual pixels is matched to the next image, so that the segmentation can then be transferred from the first image. However, the method is highly complex owing to the material data and equations of motion that are required.

SUMMARY

An object of at least one embodiment of the present invention is to specify a method for segmentation of anatomical structures, in particular of the coronary vascular system, from a sequence of 3D image data records recorded in a time sequence, which can be carried out with less time being consumed and less computation complexity, and which produces more reliable results.

At least one object may be achieved by a method. Advantageous refinements of the method can be found in the following description as well as the example embodiments.

In at least one embodiment of the present method for segmentation of anatomical structures, in particular of the coronary vascular system, from a sequence of 3D image data records recorded in a time sequence, the anatomical structure is first of all segmented from a first of the 3D image data records. This can be done in a known manner using one of the techniques mentioned in the introduction to the description. However, of course, it is also possible to use known anatomical relationships to restrict the search area for the segmentation process, even in this segmentation process.

At least one embodiment of the present method is distinguished in particular in that such known anatomical relationships as well as results from the segmentation from a 3D image data record which is in each case close in time in the sequence, in particular being immediately adjacent, are taken into account for the segmentation process from other 3D image data records. In this case, the known anatomical relationships include three-dimensional relationships between the structure to be segmented and anatomical objects located in the surrounding area. These fundamentally known anatomical relationships make it possible to considerably restrict the search areas for carrying out the segmentation process, and/or to use segmentation parameters associated with the three-dimensional relationships.

This in its own right leads to a reduction in the time consumption and computation complexity for carrying out the segmentation process. In addition, the result of the segmentation from an image data record close to this in time, in general of the immediately preceding adjacent image data record, is taken into account in at least one embodiment of the present method. This makes use of the fact that, for example in the case of a 4D image data record of one heart cycle, the coronary vessels cannot move indefinitely between two successive 3D image records.

The search in the volume data record for elements which possibly represent parts of the coronary vascular system is thus considerably restricted and speeded up. Furthermore, the inclusion of anatomical knowledge and of the segmentation results calculated in the previous time step considerably improves the reliability of the segmentation result, and thus the diagnostic value of the segmented structures.

In many known methods from the prior art, the segmentation from a 3D image data record in a time sequence is carried out completely independently of previous segmentation results from 3D image data records in the same sequence. By way of example, existing methods in each case consider only the representative gray-scale values of the vessels, per se, in each case, for example during the segmentation of the coronary vessels. Anatomical relationships, such as the position and distance between the coronary vessels and the myocardium are ignored in this process. In the case of the known methods, this has quite often led to the disadvantage of the segmentation result including regions which have no relationship whatsoever with the coronary vessels. One representative example in this case is a conventional region growing algorithm, which quite frequently extends into adjacent tissue and thus produces a corruptive result without previous knowledge.

In contrast, in the case of at least one embodiment of the present method, the segmentation is not carried out, as in the case of the existing algorithms, independently from time step $t_i$ to time step $t_{i+1}$ in the 3D image data records. In fact, it is based on an initial and thus given coronary vascular system segmentation of a first 3D image data record for the time $t_0$, before then passing directly to the next 3D image data record or to time step $t_1$, with the results $S(t_0)$ from this segmentation process being included directly. At the same time, known anatomical relationships, that is to say anatomical knowledge, are included in the segmentation process for the next time steps.

For this purpose, at least one anatomically significant point or at least one anatomically significant surface whose relationship with the structures to be segmented is fundamentally known is preferably segmented, or at least defined therein, in advance from the initial 3D image data record. If the respective current distance is known during the segmentation of these anatomically significant points or surfaces, the search area for the segmentation process is then correspondingly limited.

This is preferably done by definition of individual support points within the initially segmented structure, from each of which the search area for the segmentation from the next 3D image data record is defined on the basis of the position and the distance to the identified points or surfaces. After the segmentation from the respective next 3D image data record, new support points are defined again from the respective next 3D image data record, in a corresponding manner in the structure that has been segmented from this image data record.

This allows the segmentation process to be carried out using all the 3D image data records in a sequence. However, of course, it is also possible to omit individual 3D image data records from the sequence, so that the results of the next image data record in time from which the structure has already been segmented are then in each case included in the segmentation from a 3D image data record.

The anatomical relationships may be taken into account, for example, by referring to a table that is provided, in which predetermined segmentation parameters and/or a predetermined search area are/is in each case associated with different distances to the anatomically significant point and/or the anatomically significant surface for a known model topology, that is to say for known anatomical relationships. In this case, the expression segmentation parameters means, for example, threshold values for the segmentation process, which can also be changed with the distance to the significant points or surfaces, in order to improve the segmentation result.

Although the main field of application of at least one embodiment of the present method represents the segmentation of anatomical vessel structures in the 4D image data record of a CTA image record, at least one embodiment of the method can also be used for segmentation of other anatomical structures in 4D image data records from other imaging techniques, such as MR, PEP, SPECT or 3D ultrasound, provided that suitable segmentation parameters are available for a segmentation process.

BRIEF DESCRIPTION OF THE DRAWINGS

The method will be explained once again in the following text using one example embodiment and in conjunction with the drawings, in which:

FIG. 2 shows an example of the step from the initial segmentation to the segmentation from the next 3D image data record according to at least one embodiment of the present method.

DETAILED DESCRIPTION OF THE EXAMPLE EMBODIMENTS

Figure 1:
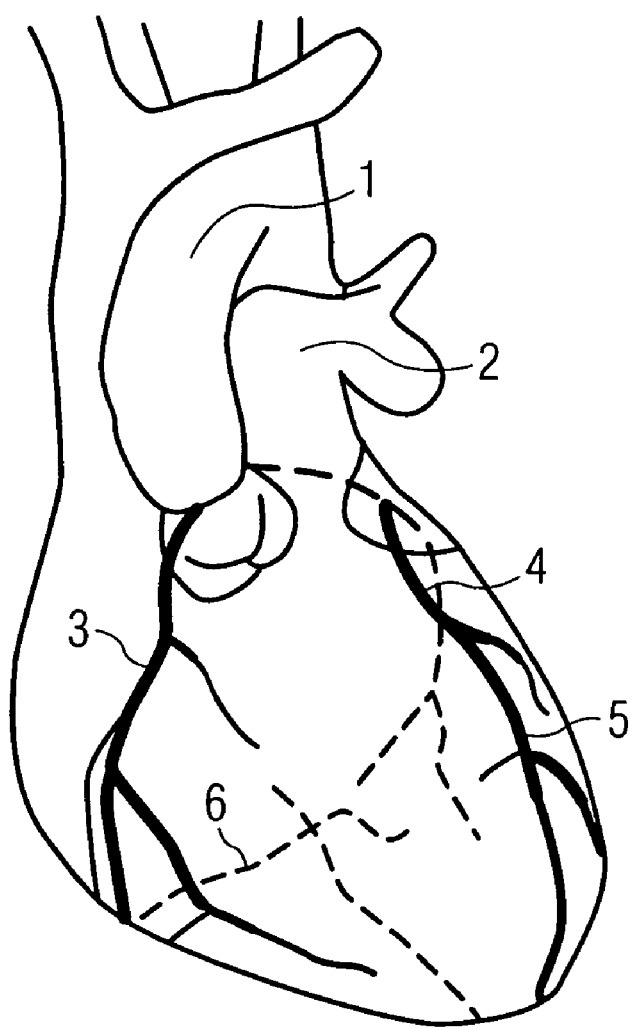
FIG. 1 shows an example of the position of the coronary vessels along the myocardium.
Figure 1:
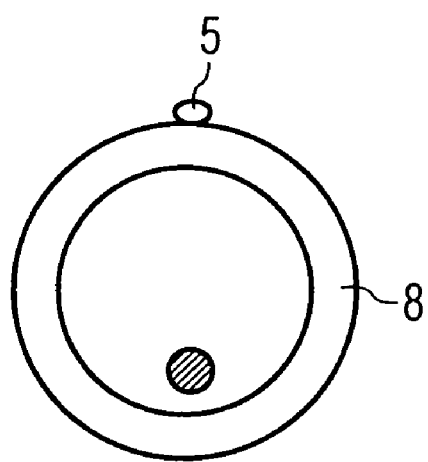

For illustrative purposes, the upper part of FIG. 1 shows a schematic illustration of the heart in which, by way of example, the aortic arch 1, the pulmonary artery 2, the front branch of the right-hand coronary artery 3 (RCA), the front branch of the left-hand coronary artery (LCA) 4, the side branch of the left-hand coronary artery (LAD) 5 and the rear branch of the right-hand coronary artery (RCA) 6 can be seen. The rear branches are in this case each represented by dashed lines. This clearly shows that the movement of the coronary vessels between the heart phases must be restricted owing to the anatomical circumstances. The vessels in this case always run along the myocardium, which considerably restricts the search area.

In this context, the lower example illustrates the side branch of the left-hand coronary artery 5, which is moving above the myocardium 8.

At least one embodiment of the present method makes use of this anatomical relationship and of the known anatomical relationships during heart movement in order to restrict the search area for segmentation on the basis of the known three-dimensional relationship between the coronary arteries and the myocardium. In the present example, the segmented vessels are for this purpose subdivided into different support points $P_i$, from each of which a permissible search area R is defined. The process of restricting this search area R takes into account the fact that the support points $P_i$ can move only within a specific area from one heart phase to the next. Furthermore, a distance d from the myocardium must always be maintained.

In the present example, a 4D image data record of the heart is provided, which is intended to be segmented in accordance with at least one embodiment of the present method. The procedure for this segmentation process is illustrated in FIG. 2, which shows the first step of the initial segmentation $S(t_0)$ as well as the subsequent second step of segmentation $S(t_1)$ of a subsequent 3D image data record.

First of all, the coronary vessels are segmented from the first 3D image data record in the present sequence, which corresponds to the time $t_0$, for example the diastole, using conventional methods. The segmented coronary vessels are illustrated in a highly schematic form in the left-hand part of FIG. 2, which shows the front branch of the left-hand coronary artery 4, the side branch of the left-hand coronary artery 5 and the rear branch of the left-hand coronary artery 7.

After this initial segmentation, which can be carried out using the conventional segmentation algorithms, suitable support points $P_1$ to $P_4$ are defined in the segmented coronary vascular system, as can be seen in the figure. Furthermore, a heart model is generated from this 3D image data record by segmentation of the left-hand and right-hand ventricle, and of the myocardium. The distances between the support points $P_1$ to $P_4$ and the myocardium and/or the left-hand ventricle are then calculated.

After this initial segmentation $S(t_0)$, the 3D image data record which corresponds to the next time $t_1$ within the heart phase is segmented. This is illustrated in the right-hand part of the figure. In this case, a search area R is defined for each of the defined support points $P_1$ to $P_4$, for example a sphere with a fixed radius which is defined on the basis of the maximum possible movement of the coronary vessels from the time $t_0$ to the time $t_1$, as well as the minimum distance to the myocardium.

Image processing methods are now used to search for candidates for each support point in the 3D volume data record which could be a representative of a vessel. The search process in each case takes account of the search area R defined around each support point, including the distance d to the previously segmented myocardium, the left-hand ventricle or the right-hand ventricle. The position of the myocardium 8 is in this case shown in the right-hand part of the figure, in the same way as the distance d as well as the search area R for one of the support points.

The segmentation process itself can once again be carried out taking into account the search area and the distance using known segmentation techniques. It is thus also possible to use the conventional region growing technique, provided that the restrictions mentioned above are taken into account. Further optimization steps, such as compliance with smoothness conditions or consideration of anatomical branches, can additionally be taken into account in this process, as well.

After the complete segmentation of the coronary vessels from the image data record for the time $t_1$, the coronary vessels are segmented from the 3D image data record for the next time $t_2$. This is done in the same way, but on this occasion making use of the segmentation results from the 3D image data record for the time $t_1$. The entire method is in this case carried out successively with all of the 3D image data records in the present sequence from which the coronary vascular system is intended to be segmented.

The use of both known anatomical relationships, in particular with respect to the location of the coronary vessels, and of the segmentation results from the respective previous time for the calculation in the next time allows the segmentation of the coronary vessels from the entire 4D image data record to be carried out considerably more quickly than is the case with the known techniques. Furthermore, the use of the above information makes it possible to achieve a considerably more reliable segmentation result.

The above described embodiments of the method may further be embodied in a physical device, as would be understood by one of ordinary skill in the art, including via use of the disclosed and/or illustrated examples.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for segmentation of anatomical structures from a sequence of 3D image data records recorded in a time sequence, comprising:
   initially segmenting, by a computing device, an anatomical structure from a first of the 3D image data records, during the segmentation of the anatomical structure in further 3D image data records, at least one of a plurality of search areas of the segmentation being restricted and segmentation parameters associated with the three-dimensional relationships from other 3D image data records being used, on the basis of known spatial conditions of the structure to be segmented, with respect to anatomical objects located in the surrounding area and of results of the segmentation from a respective previous 3D image data record in the sequence from which the structure has already been segmented, wherein
   at least one of at least one known anatomically significant point and at least one known anatomically significant surface is identified in the first 3D image data record, and wherein a distance relative to at least one of the anatomically significant point and the anatomically significant surface is taken into account in the restriction of the search areas and defined at a minimum.

2. The method as claimed in claim 1, wherein support points in the respectively segmented anatomical structure are defined after the segmentation of the anatomical structure from the first 3D image data record and the further 3D image data records, from which support points the search areas for the segmentation of the anatomical structure are defined in the 3D image data record which is then subjected to segmentation.

3. The method as claimed in claim 1, wherein a surface of at least one of the ventricles and the myocardium is identified as a known anatomically significant surface in the 3D image data record, and is segmented in advance, for the segmentation of a coronary vascular system from the first 3D image data record.

4. The method as claimed in claim 1, wherein the method is for segmentation of anatomical structures of the coronary vascular system, from a sequence of 3D image data records recorded in a time sequence.

5. The method as claimed in claim 2, wherein a surface of at least one of the ventricles and the myocardium is identified as a known anatomically significant surface in the 3D image data record, and is segmented in advance, for the segmentation of a coronary vascular system from the first 3D image data record.

6. A method for segmentation of anatomical structures from a sequence of 3D image data records recorded in a time sequence, comprising:

initially segmenting, by a computing device, an anatomical structure from a first of the 3D image data records, during the segmentation of the anatomical structure in further 3D image data records, at least one of a plurality of search areas of the segmentation being restricted and segmentation parameters associated with the three-dimensional relationships from other 3D image data records being used, on the basis of known spatial conditions of the structure to be segmented, with respect to anatomical objects located in the surrounding area and of results of the segmentation from a respective previous 3D image data record in the sequence from which the structure has already been segmented, wherein at least one of at least one known anatomically significant point and at least one known anatomically significant surface is identified in the first 3D image data record, and wherein a distance relative to at least one of the anatomically significant point and the anatomically significant surface is taken into account in the restriction of the search areas, and at least one of the segmentation parameters and the search areas is associated with different distances to at least one of the anatomically significant point and the anatomically significant surface in a table.

* * * * *